US00PP09173P

United States Patent [19]

Howard

[11] Patent Number: Plant 9,173

[45] Date of Patent: Jun. 20, 1995

[54] APRICOT TREE—EARLI SUN CULTIVAR

[75] Inventor: George T. Howard, Selma, Calif.

[73] Assignee: Stark Brothers Nurseries and Orchards Company, Louisiana, Mo.

[21] Appl. No.: 303,511

[22] Filed: Sep. 9, 1994

[51] Int. Cl.[6] ..... A01H 5/00

[52] U.S. Cl. ..... Plt./39

[58] Field of Search ..... Plt. 39

[56] References Cited

PUBLICATIONS

Ramming, D. W., et al., "'Castlebrite' Apricot" *Hortscience* 13(4):485. 1978.

*Primary Examiner*—James R. Feyrer

*Attorney, Agent, or Firm*—Burns, Doane, Swecker & Mathis

[57] ABSTRACT

A new and distinct variety of apricot tree is provided which originated as a single bud sport or limb mutation of the 'Castlebrite' cultivar (non-patented in the United States). The new cultivar has been named 'Earli Sun', and can be distinguished by its freestone fruits which are substantially similar in color and appearance to those of 'Castlebrite' cultivar, yet are significantly larger in size, being ripening approximately two days later than those of the 'Castlebrite' cultivar, and are markedly lower in the acidity of the flesh at harvest.

2 Drawing Sheets

BACKGROUND OF THE INVENTION

The 'Castlebrite' apricot (non-patented in the United States) was introduced in 1978 and has been met with much interest by commercial fruit growers in the San Joaquin Valley of California since its harvest date commonly precedes that of other apricot varieties grown in that area. See in this regard the article by D. W. Ramming and O. Tanner entitled 'Castlebrite' Apricot appearing in HortScience 13(4):485 (1978). Accordingly, the 'Castlebrite' apricot because of its early fruit maturity date has aided commercial growers, and currently represents one of major cultivars that is being grown to yield an early season apricot crop in California in spite of its recognized small fruit size and the marked tartness of the resulting fruit crop. Historically higher prices are reaized by growers who are able to supply the early season fresh fruit market, and there has been an ongoing quest to find new cultivars that exhibit commercially significant improved traits as well as an early harvest date.

SUMMARY OF THE INVENTION

The new apricot cultivar of the present invention was discovered during May of 1986 as a single bud sport or limb mutation of unknown causation that appeared on one of three main scaffolds of a four year-old tree of the 'Castlebrite' cultivar located in an orchard of such variety situated on the northwest corner of Clarkson and Temperance Avenues near the City of Selma, County of Fresno, State of Calif. Had I not discovered and preserved the new cultivar of the present invention it would have been lost to mankind. Initially I was primarily attracted to the new variety because the distinctly larger fruit that it consistently exhibited.

It has been found and confirmed upon further testing that the new apricot cultivar of the present invention:

(a) forms early-maturing fruit on a consistent basis that is larger in size than that of the 'Castlebrite' cultivar, (b) forms fruit of low to mild acidity that is of a significantly lesser acidity than that of the 'Castlebrite' cultivar, and (c) exhibits a growth habit that is more vigorous than that of the 'Castlebrite' cultivar.

Many other characteristics of the new variety are substantially identical to those of the parent 'Castlebrite' cultivar.

The fruit of the new variety has been found to average approximately 70 to 100 percent larger in the axial and transverse diameters than the fruit of the 'Castlebrite' variety. The fruit of the new variety has been observed to mature approximately two days later than that of the 'Castlebrite' variety. The fruit flesh of the new vareity is noticeably lesser in acidity and thereby lacks the tartness of the 'Castlebrite' variety as is readily apparent by subjective organoleptic evaluation. It has been found that the stone of the new variety is free of the flesh when eating ripe, but is considered to be only semi-free near the basal one-half of the pit when ready for commercial fresh fruit harvest, whereas the stone of the 'Castlebrite' variety tends to be free at both stages of ripeness.

The pattern of fruit reipening between the new variety and the 'Castlebrite' variety tends to be different. More specifically, the fruit of the new variety begins to ripen near the pit and commonly requires a greater length of time for the entire flesh to ripen. This commonly is demonstrated by the longer time required for the development of the flesh color from pale greenish-yellow to orange throughout the entire flesh. Accordingly, the new variety can be harvested with more green skin coloration being present than the 'Castlebrite' variety.

In a side-by-side comparison planting, the new variety has been observed to yield heavy crops over a six year period, whereas the parent 'Castlebrite' variety has produced light crops in two of those years thereby suggesting that the new variety may crop more consistently than the 'Castlebrite' variety.

The growth habit of the new variety tends to be more vigorous than that of 'Castlebrite' variety. Also, the new variety tends to form larger leaves than the parent 'Castlebrite' variety. Additionally, in early Spring, the current season's vegetative growth of the new variety tends to be more orange-yellow in coloration than that of the 'Castlebrite' variety. This difference in the coloration of the vegetative growth becomes indistinguishable as the season progresses.

Although the causation of the mutation that produced the new variety is unknown, such mutation may have been the result of an increase in ploidy that has resulted in the creation of the more vigorous tree and fruit character. However, reductions in fertility that often are exhibited by polyploids have not been manifested in the fruit set of the new variety and the cropping ability to date has been more than adequate. Seed viability and the chromosomal compliment have not been investigated.

The new variety of the present invention has been asexually reproduced by budding onto Nemaguard peach rootstock beginning in lae May of 1986. During the following winter, the resulting trees were dug and were transplanted to a different orchard site near the intersection of Conejo and Fowler Avenues, south of the City of Selma, County of Fresno, State of California. The asexually reproduced trees were planted adjacent to comparable trees of the 'Castlebrite' variety that were also propagated onto the same Nemaguard peach rootstock. Fruiting observations beginning in 1989 and thereafter, have shown that the characteristics of the asexually reproduced trees are stable and are identical to those of the original mutated limb and in the indicated respects are substantially different than those of the parent 'Castlebrite' variety.

The new cultivar has been named the 'Earli Sun' cultivar.

BRIEF DESCRIPTION OF THE PHOTOGRAPHS

The accompanying photographs show typical specimens of the new cultivar as depicted in color as nearly true as it is reasonably possible to make the same in color illustrations of this type. All specimens were obtained from trees of the 'Earli Sun' cultivar growing in an orchard located near the intersection of Conejo and flower Avenues, south of the City of Selma, County of Fresno, State of Calif.

FIG. 1 illustrates typical foliage and mature fruit of 'Earli Sun' apricot of the present invention that was harvested on May 14, 1992 with some of the fruit being divided along the suture plane so as to reveal the flesh color and the freeness of the pit. The photograph was taken on May 22, 1992 following the cold storage of the fruit.

FIG. 2 illustrates at the left five mature fruits of the parent 'Castlebrite' apricot that were harvested on May 14, 1992, and at the right five mature fruits of the new 'Earli Sun' apricot that were harvested on May 17, 1992. The photograph was taken on May 22, 1992 following the cold storage of the fruits. Significant differences in fruit size, and the similarity in fruit coloration are apparent. The fruit coloration is velieved to be more accurately depicted in FIG. 1 than in FIG. 2.

FIG. 3 illustrates at the left the more vigorous growth habit of a typical 'Earli Sun' tree, when compared at the right to that of a typical 'Castlebrite' tree. The photograph was taken on Jun. 4, 1994.

DETAILED DESCRIPTION

The following is a detailed description of the new cultivar that is based upon the observation of trees grown at and fruit harvested from the previously-identified orchard located near the intersection of Conejo and Fowler Avenues, south of the City of Selma, County of Fresno, State of Calif. Color designations are with reference to Inter-Society Color Council—National Bureau of Standards Centroid Color Charts.

TREE

Size: Large.

Figure 3:
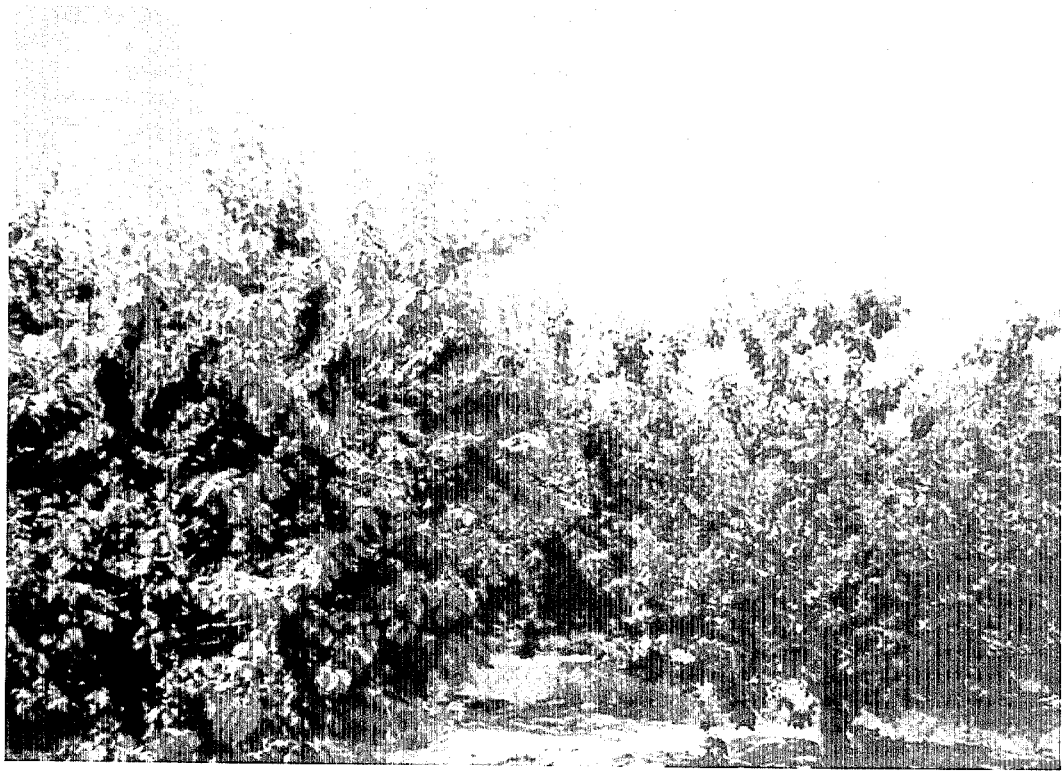

Growth habit: Moderately upright, similar to but generally more vigorous than that of 'Castlebrite' as illustrated In FIG. 3.

Productivity: Very good.

Cropping: Consistent, and heavy.

Trunk:

*Color.*—Reddish Grey Brown (47-d-gy-r. Br).

*Surface characteristics.*—Some long vertical fissures exposing lighter colored bark underneath with many diagonally connecting fssures.

Branches:

*Size.*—Medium.

*Color.*—Reddish Grey Brown (47-d-gy-r. Br).

*Surface characteristics.*—Texture: Smooth, and glabrous. Lenticels: Number: Approximately 10 to 14 per square inch. Color: Reddish Brown (72-d-oy). Size: Approximately 3 to 4 mm in length.

Leaves:

*Size.*—Large.

*Length.*—Approximately 70 to 102 mm.

*Width.*—Approximately 50 to 75 mm.

*Shape.*—Broadly ovate with acuminate leaf tip.

*Color.*—Dorsal: Dark Green (125 m.ol. G). Ventral: Grey Green (120 m.y. G).

*Marginal configuration.*—Finely serrate.

*Petiole.*—Length: Approximately 30 mm. Thickness: Approximately 1 to 2 mm.

*Stem glands.*—Number: Commonly one to four. Arrangement: Opposite to alternate. Size: Very small (approximately 0.2 mm). Shape: Globose.

FLOWER

Dormant buds:

*Size.*—Approximately 5 mm in length, and approximately 3 to 4 mm in width.

*Surface texture.*—Lightly pubescent.

Flowers:

*Date of bloom.*—First bloom: Was noted on Feb. 16, 1992. Ninety percent open: Was noted on Feb. 25, 1992. Petal fall: Was noted on Mar. 3, 1992.

*Size.*—Medium, and approximately 25 mm in diameter at anthesis.

*Petals.*—Approximately 15 mm in length, and approximately 9 mm in width.

*Color.*—Purple Red (248 deep P Pk) at bud-break, and maturing to Border White (263 white) at anthesis.

*Number of pistils.*—1.

*Number of stamens.*—Approximately 26 to 30.

FRUIT

Maturity: Approximately May 15 to 25 at Selma, Calif.

Size: Uniformly large.

*Axial diameter.*—Approximately 50 to 54 mm.

*Transverse diameter in suture plane.*—approximately 47 to 50 mm.

*Transverse diameter at right angles to suture plane*-.—Approximately 50 to 54 mm.

Figure 1:
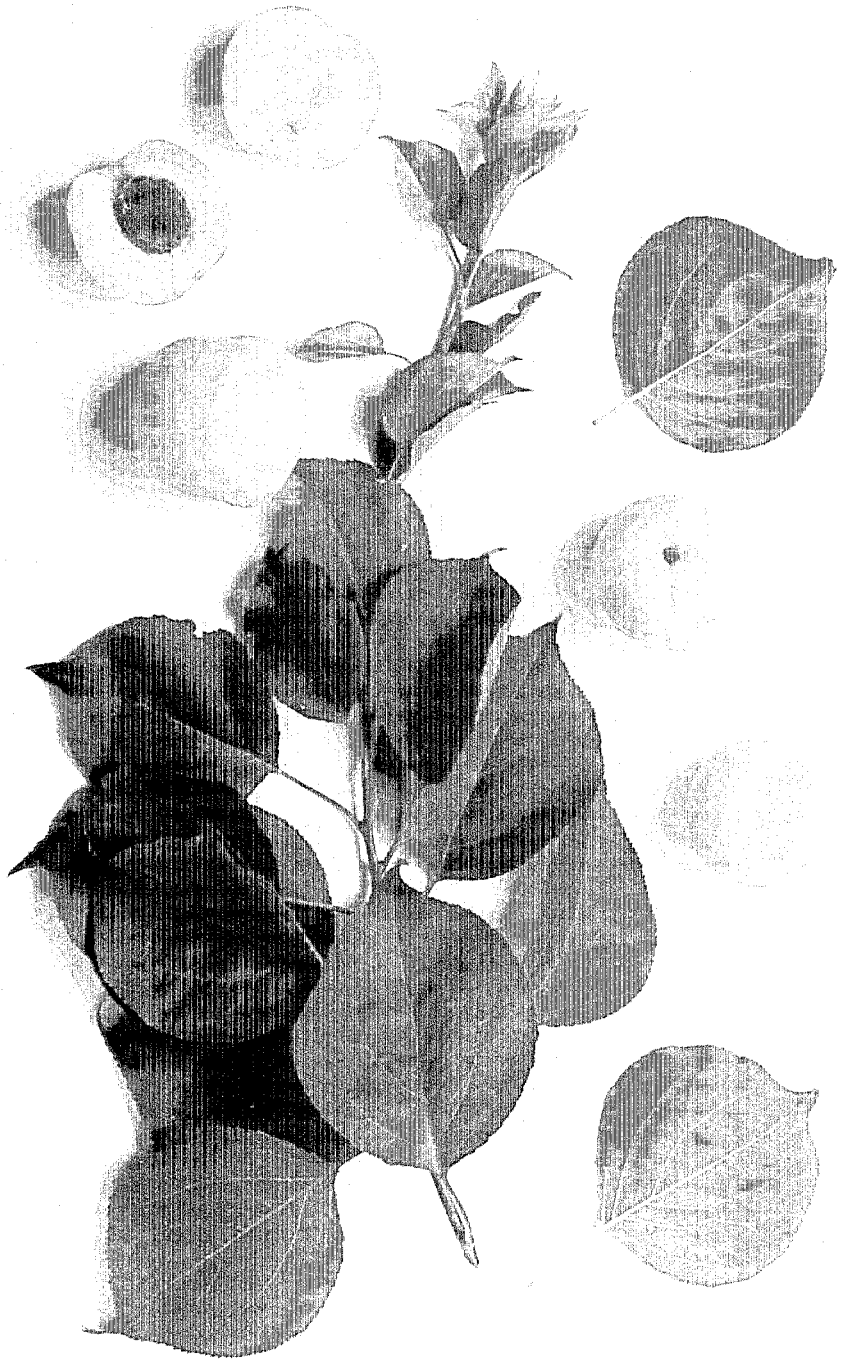
Figure 2:
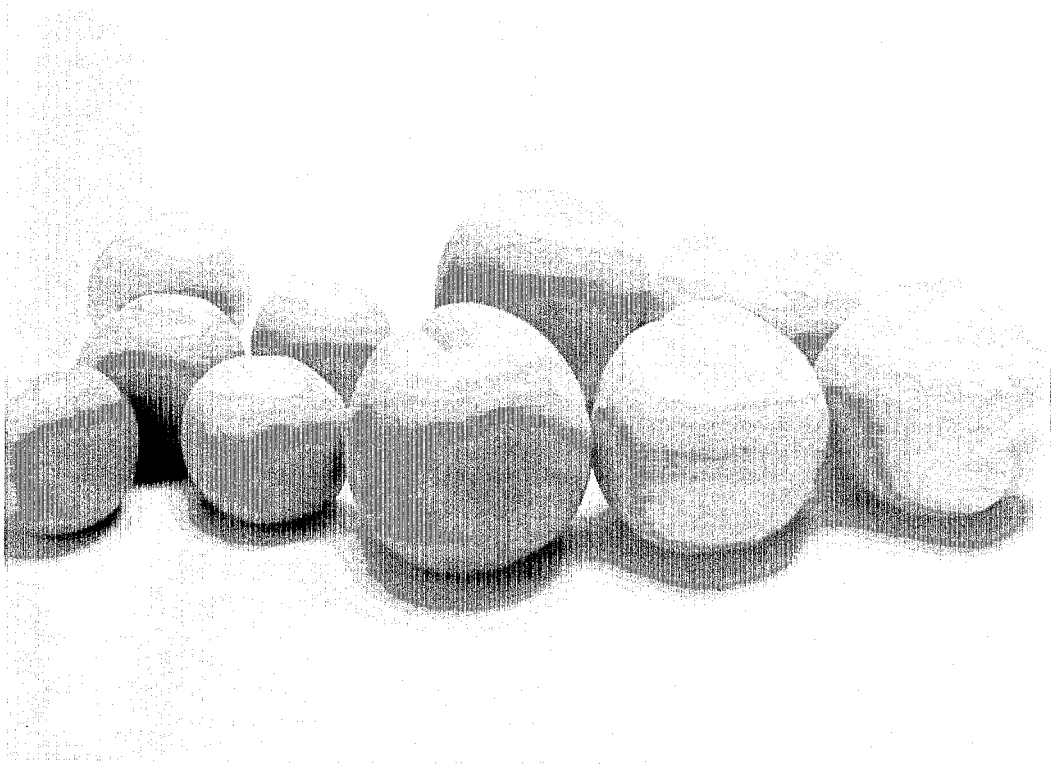

Form: Shape among fruits tends to be substantially uniform as illusrated in FIG. 2.

*Symmetry.*—Ovoid, slightly truncate with slightly uneven sides.

*Suture.*—Distinct, slightly depressed, approximately 82 to 94 mm in length, and commonly does not extend to the opposite side of the stem cavity or pistil tip.

*Stem cavity.*—Rounded shoulders, round in cross section, approximately 10 mm in breadth×approximately 10 mm in width×approximately 10 mm in depth.

*Base.*—Smoothly rounded.

*Apex.*—Rounded-shoulders and slightly depressed (approximately 3 to 4 mm).

*Pistil tip.*—Depressed, and generally not apparent.

*Stem.*—Length: Approximately 10 mm. Caliper: Approximately 10 mm.

*Skin.*—Thickness; Medium. Surface: Smooth. Tendency to crack: No cracking has been observed.

*Color.*—Slightly greenish at harvest, ripening to Bright Yellow (67 Brill OY), and eventually to Orange Yellow (50 s 0) when fully mature.

*Pubescence.*—Scantly pubescent.

Flesh:

*Color.*—Orange Yellow (71 m. oy) and (50 s. 0).

*Surface of pit cavity.*—Smooth.

*Color of pit well.*—Yellow brown (48 v. 0).

*Juice.*—Moderately juicy.

*Flavor.*—Sub-acid, mild, with complexing similar to 'Castlebrite'.

*Aroma.*—Mildly aromatic, similar to 'Castlebrite'.

*Texture.*—Fine-grained, meaty, and slightly fibrous.

*Ripening.*—From pit cavity outwards towards the skin.

*Eating quality.*—Good, and except for significantly lower acidity is substantially similar to that of 'Castlebrite'.

Stone: Freestone when eating ripe.

*Size.*—Medium. Axial diameter: approximately 33 mm. Transverse diameter in suture plane: approximately b 31 mm. Transverse diameter at right angles to suture plane: approxiamtely 18 mm.

*Form.*—Obovate, and slightly flattened at base and rounded at apex with no apparent apical tip.

*Sides.*—very slightly pitted.

*Dorsal suture.*—Wide, raised, and slightly winged.

*Color.*—Dark brown (61 gy. Br).

Use: Fresh market.

Keeping quality: Good.

Shipping quality: Good.

Resistance to insects and diseases: Substantially similar to 'Castlebrite'.

I claim:

1. A new and distinct cultivar of apricot tree having the following combination of characteristics:

(a) forms early-maturing fruit on a consistent basis that is larger in size than that of the 'Castlebrite' cultivar, (b) forms fruit of low to mild acidity that is of a significantly lesser acidity than that of the 'Castlebrite' cultivar, and (c) exhibits a growth habit that is more vigorous than that of the 'Castlebrite' cultivar;

substantially as shown and described.

* * * * *